(12) United States Patent
Katz

(10) Patent No.: US 7,313,220 B2
(45) Date of Patent: Dec. 25, 2007

(54) DESIGN FOR REALIZING AN ONLINE ELEMENT ANALYSIS

(76) Inventor: Elisabeth Katz, Ahornweg 8, D-72226 Simmersfeld (DE)

( * ) Notice: Subject to any disclaimer, the term of this patent is extended or adjusted under 35 U.S.C. 154(b) by 151 days.

(21) Appl. No.: 10/519,383

(22) PCT Filed: Jul. 3, 2003

(86) PCT No.: PCT/DE03/02224

§ 371 (c)(1),
(2), (4) Date: Dec. 27, 2004

(87) PCT Pub. No.: WO2004/008128

PCT Pub. Date: Jan. 22, 2004

(65) Prior Publication Data

US 2005/0232391 A1    Oct. 20, 2005

(30) Foreign Application Priority Data

Jul. 10, 2002    (DE)    ............................ 102 30 990

(51) Int. Cl.
*G01N 23/223*    (2006.01)
(52) U.S. Cl. ............................. 378/44; 378/45; 378/47
(58) Field of Classification Search ............. 378/44, 378/45, 47, 50
See application file for complete search history.

(56) References Cited

U.S. PATENT DOCUMENTS

| | | | | |
|---|---|---|---|---|
| 2,763,784 A * | 9/1956 | Webster | ........................ | 378/50 |
| 2,837,656 A * | 6/1958 | Hendee et al. | ................. | 378/49 |
| 3,327,584 A * | 6/1967 | Kissinger | .................... | 356/614 |
| 3,655,964 A | 4/1972 | Slight et al. | | |
| 5,192,869 A * | 3/1993 | Kumakhov | ................. | 378/145 |
| 5,305,366 A * | 4/1994 | Nakahara et al. | .............. | 378/45 |
| 5,497,008 A | 3/1996 | Kumakhov | | |
| 5,721,759 A | 2/1998 | Raatikainen | | |
| 5,754,620 A * | 5/1998 | Hossain et al. | ................ | 378/45 |
| 5,778,039 A | 7/1998 | Hossain et al. | | |
| 5,974,111 A | 10/1999 | Krug et al. | | |
| 6,233,306 B1 | 5/2001 | Van Sprang | | |
| 6,965,663 B2 * | 11/2005 | Ohzawa | ........................ | 378/44 |
| 2001/0021240 A1 * | 9/2001 | Kojima et al. | ................. | 378/45 |

FOREIGN PATENT DOCUMENTS

DE    291420 A  *  6/1991

(Continued)

OTHER PUBLICATIONS

Machine Translation of DD 291420 A5.*

(Continued)

*Primary Examiner*—Chih-Cheng G Kao
(74) *Attorney, Agent, or Firm*—Rabin & Berdo, PC

(57) ABSTRACT

A device for realizing an online element analysis for a substance (S) that is conveyed past or flows past a measuring station is provided with a device for conveying the substance to be measured, a measuring station with an X-ray source (10), and an X-ray fluorescence detector (20) with radiation inlet. To improve the tolerance to calibration errors and a changing height of the sample surface, at least one first X-ray conductor (30) extends from the radiation inlet of the X-ray fluorescence detector in the direction of the conveying device (51).

26 Claims, 8 Drawing Sheets

FOREIGN PATENT DOCUMENTS

Figure 1:
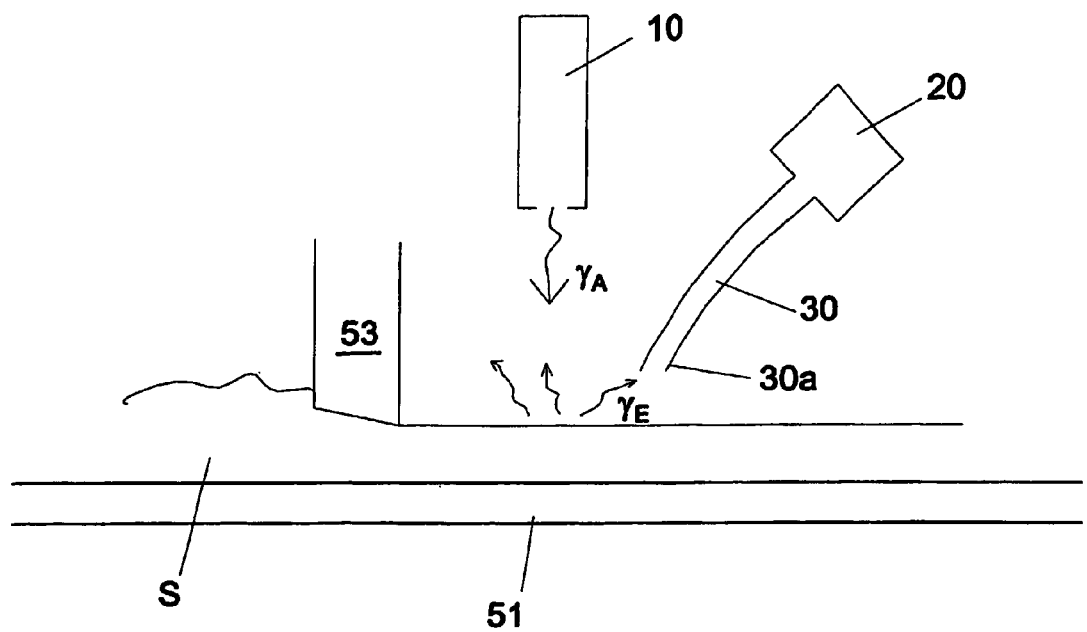

| | | |
|---|---|---|
| DE | 4408057 A1 * | 9/1995 |
| EP | 0 985 926 A2 | 3/2000 |
| EP | 1 202 045 A1 | 5/2002 |
| WO | WO 95/24638 | 9/1995 |
| WO | WO 00/16078 | 3/2000 |

OTHER PUBLICATIONS

Nikitina S V et al. : "X-Ray Fluorescence analysis on the Base of Polycapillary Kumakhov Optics" Review of scientific Instruments, American Institute of Physics. New York, US, vol. 70, No. 7, Jul. 1999, pp. 2950-2956, XP000875412. ISSN: 0034-6748.

Fiorini C et al.: "A new detection system with polycapillary conic collimator for high-localized analysis of X-ray fluorescence emission". Nuclear Science Symposium Conference Rececoed, 2000 IEEEE, US, Oct. 15, 2000, pp. 8-28-8-31, XP010556610, ISBN: 0-7803-6503-8.

Petukhov V P et al.: "X-Ray Polarizer On The Base Of Kumakhov Optics". Proceedings of the Spie, Spie, Bellingham. VA, US, vol. 3115, Jul. 31, 1997, pp. 147-152, XP009017366, ISSN: 0277-786X.

An English-language Abstract of the Japanese patent publication No. 11132970 A (May 21, 1999).

* cited by examiner

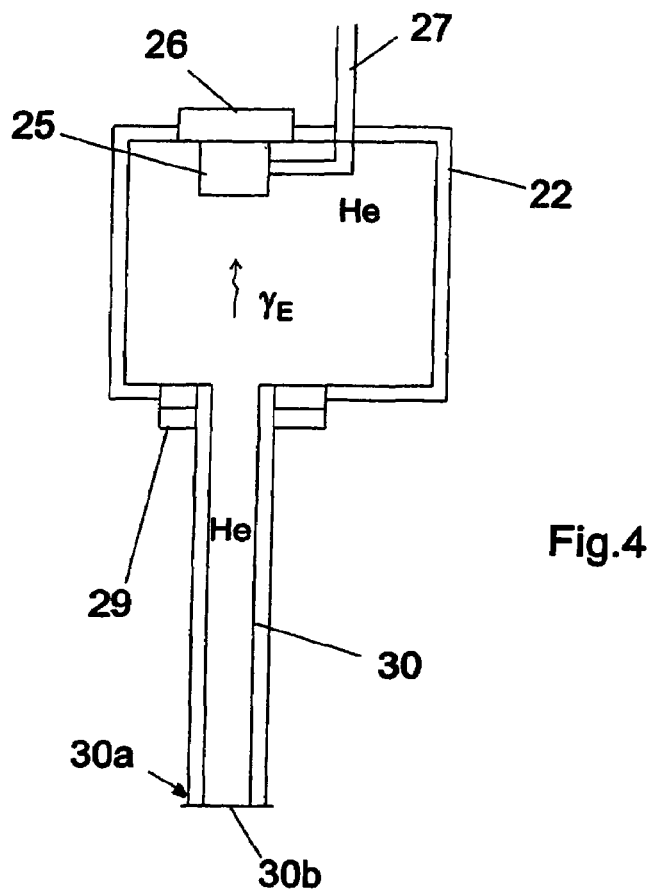
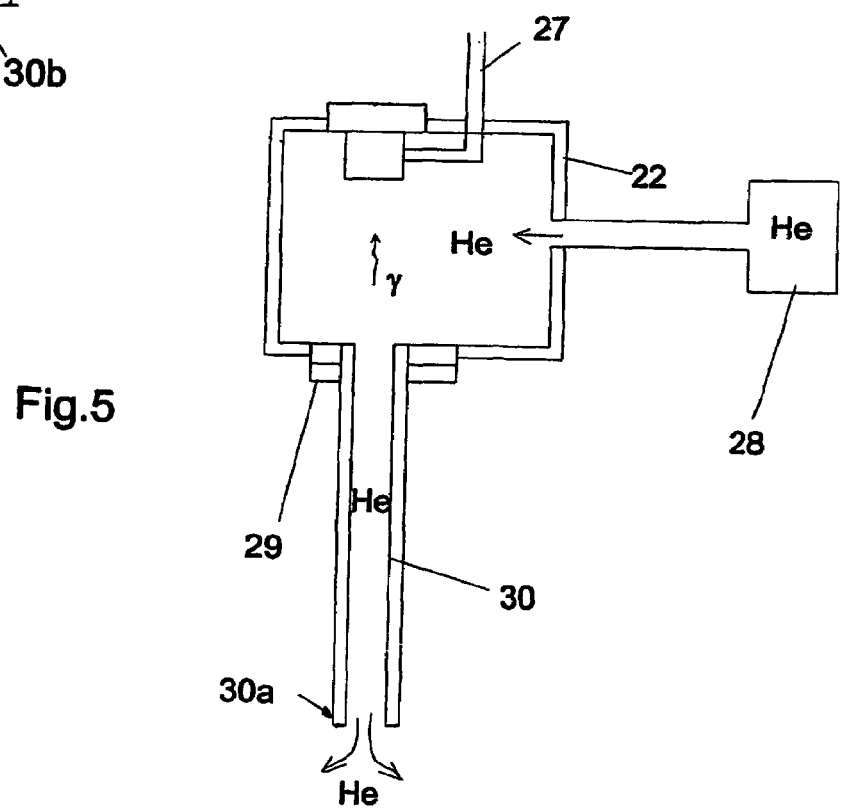
Fig.4
Fig.5

DESIGN FOR REALIZING AN ONLINE ELEMENT ANALYSIS

TECHNICAL FIELD OF INVENTION

The invention relates to a device for realizing an online element analysis.

PRIOR ART

X-ray fluorescence is a method frequently used in science and industry for measuring the share of specific elements in a sample, using X-rays to irradiate samples so as to excite specific electronic transitions in the elements of interest. With lightweight and medium lightweight elements, this relates for the most part to the $K_\alpha$ transition. The recombination of the excited transitions occurs in part radiating, wherein the energy quanta emitted in the process have a value that is characteristic for this element. For the applications of interest herein, the energy of the radiated photon generally is in the range of 1 to 30 keV. In particular at the lower end of this energy range, the emitted, soft X-rays have only a very short range in solid materials or in air, thus resulting in considerable measuring technical problems, in particular for industrial applications.

The present invention relates to a device using an online method for the X-ray fluorescence measuring. For this, the substance flow of a continuous operation is guided past a measuring station, provided with at least one X-ray source and at least one X-ray fluorescence detector. Devices of this type have numerous industrial uses, e.g. for an online analysis of coal used for an industrial process, wherein the share of ash or sulfur components or the shares of other special elements are measured. Other uses are in the steel industry to determine, for example, the share of specific elements in a still hot flow of slag.

As previously indicated, one central problem of the present measuring technique is that it is hard to detect in particular the γ-quanta at the energy-poor end of the energy spectrum of interest because of their short range in air. With offline laboratory measurements where sufficient time is available to prepare the sample accordingly and where the samples can be inserted into respective measuring apparatuses with precisely adjustable geometries, the measuring technique problems can be solved with comparative ease. However, the conditions are considerably more difficult with the applications of interest herein where in a "factory situation" measurements are taken on a substance flow having an at least slightly changing surface geometry over time, at least for some applications.

Reference PCT/US99/20867 deals with the problem of positioning an X-ray source and an X-ray fluorescence detector, used for an online element analysis, relative to a conveying device. It is suggested in this reference that the X-ray fluorescence detector be installed as close as possible to the substance to be measured, which is flowing past, in particular at a distance of less than 5 cm. Since the X-ray emission is mostly isotropic, the intensity of the X-ray fluorescence radiation naturally decreases proportional $1/r^2$, wherein the absorption in air is not even considered. Accordingly, it is fundamentally correct to say that the measurable signal is maximized if the device is arranged close to the sample. However, when realizing the suggestion put forth in the PCT/US99/20867, considerable difficulties arise, at least for some applications.

Figure 12:
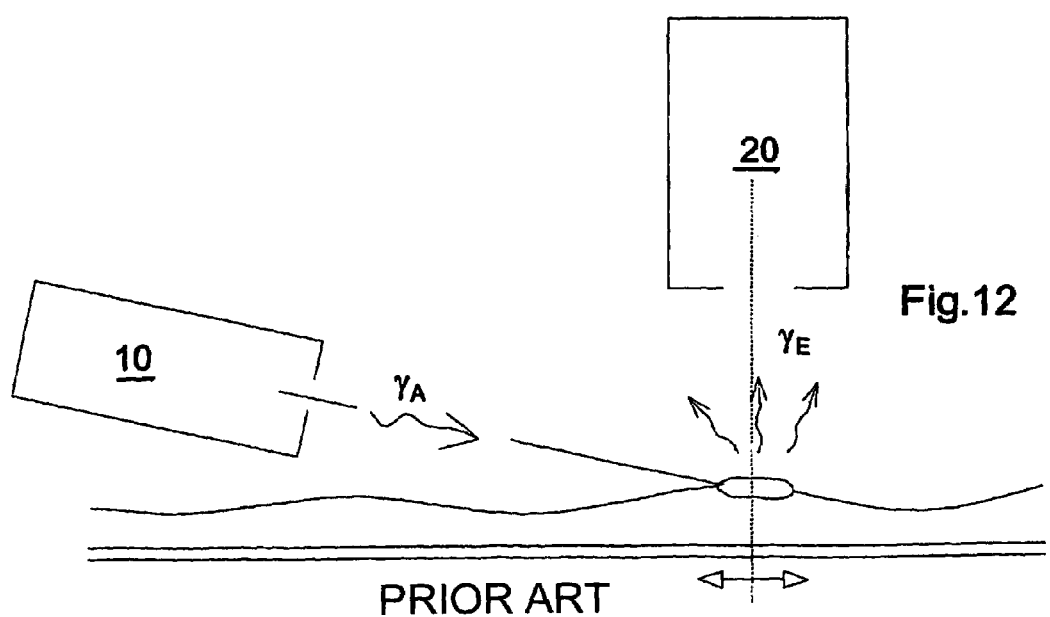

To keep the background radiation entering into the X-ray fluorescence detector as low as possible, it is generally advantageous if X-ray source and X-ray fluorescence detector are positioned on the same side of the sample, wherein this solution is generally also preferred with respect to the required output and wavelength for the X-ray source. Since X-ray source as well as X-ray fluorescence detector naturally have certain spatial dimensions, the close arrangement of the X-ray fluorescence detector to the substance to be measured generally necessitates that the radiation from the X-ray source is radiated at a relatively flat angle onto the substance that is conveyed past or flows past, for example as shown in FIG. 12. Thus, even the slightest error in adjustment or a slight change in the height of the substance surface can result in a relatively strong change in the horizontal position of the point illuminated by the X-ray source, which is thus no longer positioned ideally within the line of sight of the X-ray fluorescence detector. As a result, considerable intensity losses and, above all, considerable intensity fluctuations can occur.

A further serious problem with arranging the X-ray fluorescence detector close to the substance to be measured is that no substance with temperatures above approximately 100 degrees can be measured. Special, cooled semiconductor elements are frequently used as X-ray fluorescence detectors, which become blind near strong heat sources.

SUBJECT MATTER OF THE INVENTION

Starting with this prior art, it is the object of the present invention to modify invention of the generic type so as to improve its tolerance to errors in adjustment and changes in height of the substance surface.

According to the invention, the fluorescent radiation emitted by the substance is no longer supplied directly to the X-ray fluorescence detector, but is initially fed into at least one first X-ray conductor and is supplied via this conductor to the X-ray fluorescence detector.

Suitable X-ray conductors are known from prior art and consist of a hollow tube, for example, which mostly takes the form of a thin, hollow glass capillary, inside of which the X-radiation can propagate via total reflection. Since the X-ray conductors can have a correspondingly thin design, completely different geometries are possible as compared to the prior art. In particular, it is possible to arrange the end of the X-ray conductor near the surface of the substance to be measured, but still radiate the exciting X-rays nearly perpendicular onto the substance.

Since the intensity of the captured X-rays inside the X-ray conductor decreases only as a result of filling gas absorption, the X-ray fluorescence detector itself can be positioned relatively far from the substance flowing by. This is a considerable advantage, especially when measuring relatively hot substances where the X-ray fluorescence detector must be protected against the heat radiated by these substances. Owing to the fact that known waveguides can also have a curved design, a thermal shield can be arranged in particular between X-ray fluorescence detector and conveyor belt; claim 14.

The exciting X-radiation may also be guided via an X-ray conductor, which further facilitates the adjustment of the device and increases the tolerance to changes in the conditions.

In a preferred embodiment, the X-ray conductors used herein consist of the aforementioned glass capillaries, which are known in the technical field. X-ray conductors of this type have so far been used for local-resolution X-ray emission measurements. For the herein suggested use, these glass capillaries have the special advantage of being heat-resistant to several hundred degrees Celsius and therefore can be moved very close to the substance to be measured, even if this substance has high temperatures.

However, the use of non-capillary hollow tubes as X-ray conductors is conceivable as well.

Owing to the fact that soft X-rays with an energy below 2 keV are absorbed to a high degree by air, the hollow tubes/glass capillaries are preferably filled with hydrogen or helium, wherein helium is preferred because it is easier to handle. As a result, relatively long distances between substance and detector can be overcome, e.g. 20 to 30 cm, even when measuring low photon energies.

In an alternative embodiment, permanent filling of the glass capillary with a lightweight gas requires the glass capillary to be closed off even at the end facing the substance. Suitable windows as a rule consist of thin plastic or beryllium films with a low temperature and/or mechanical resistance and can therefore not be used for some applications. For those applications, we suggest leaving open the ends of the hollow tubes/glass capillaries and flushing them permanently with helium during the operation, wherein the flushing can also prevent foreign particles from being deposited inside the glass capillaries.

The X-ray conductors are combined to form a bundle in a preferred embodiment, which has considerable advantages with respect to handling and adjustment as well as total sensitivity.

To permit an easier interpretation and reproduction of the measuring results, it is generally necessary, or at least helpful, to know the precise vertical position of the sample surface. The use of a distance sensor is therefore suggested. Laser distance sensors are particularly suitable for this, wherein such a laser distance sensor is preferably connected to a waveguide. This waveguide may be connected to at least one of the existing X-ray conductors, so that the distance measurements are not time-displaced or location-displaced, relative to the X-ray measurement. As a result, the total accuracy of the measurement can be increased considerably.

For the parallel alignment of the X-rays, an X-ray split lens may be arranged in the beam path from the X-ray source before the radiated light hits the substance to be measured, which results in two advantages. On the one hand, the intensity radiated onto the measuring range can be increased because the radiated light no longer decreases in intensity proportional $1/r^2$ following the parallel alignment. On the other hand, no fluctuations or only slight fluctuations occur in the irradiated intensity when the height of the sample surface changes, which cannot be avoided particularly with large-grain samples, thus permitting an easier interpretation of the measuring results.

SHORT DESCRIPTION OF THE DRAWINGS

Figure 2:
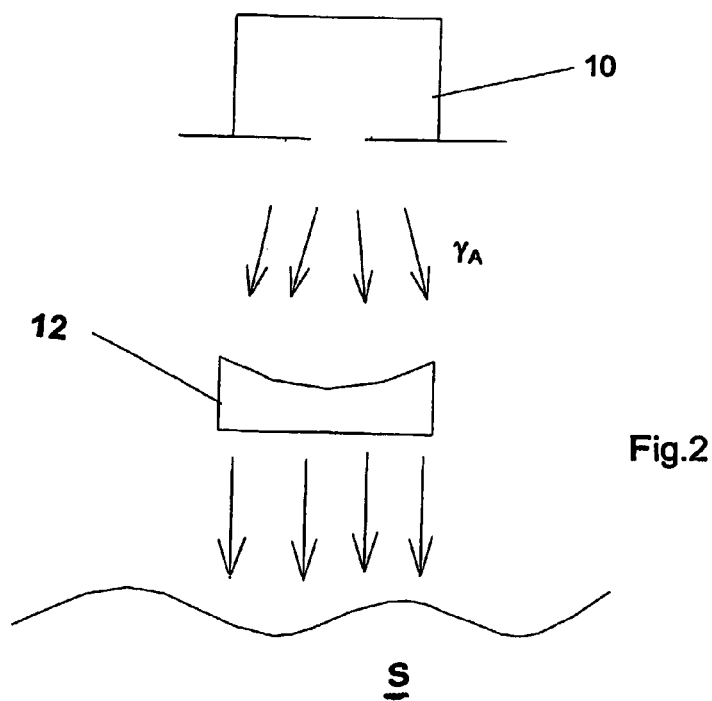
Figure 3:
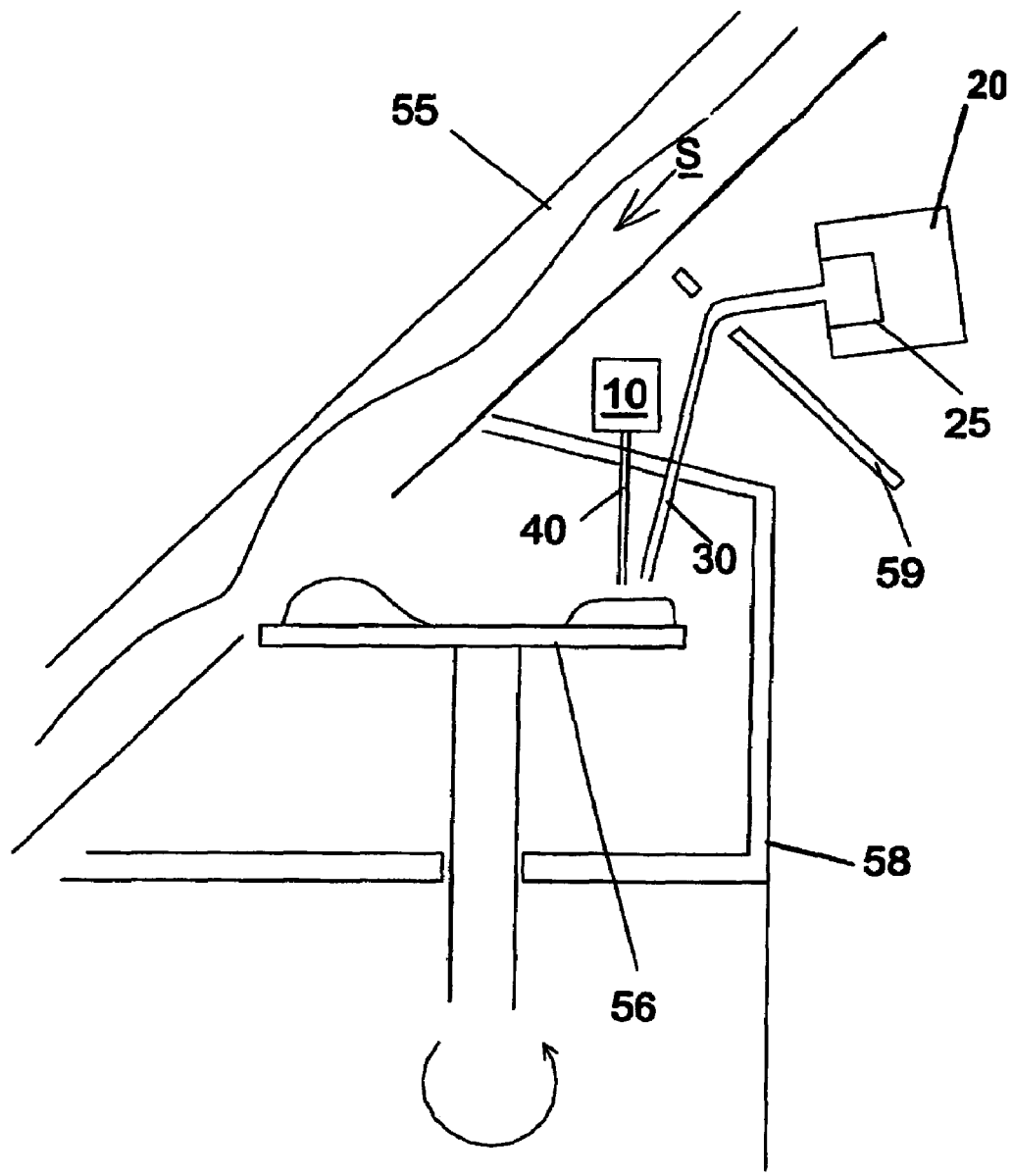
Figure 6:
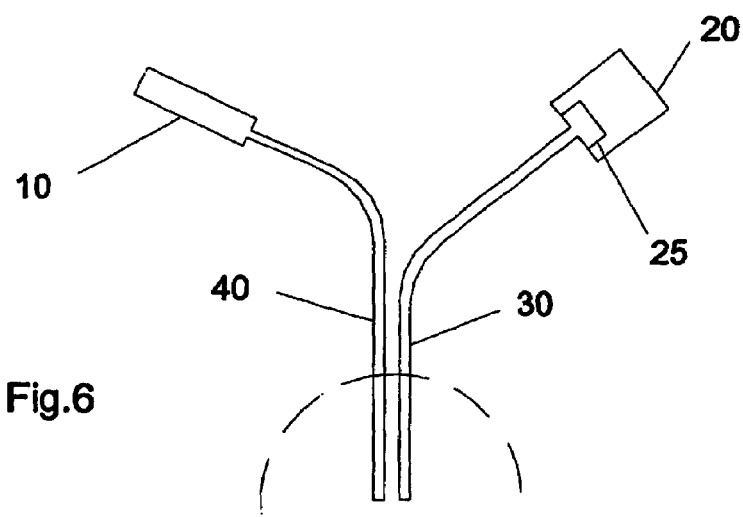
Figure 7:
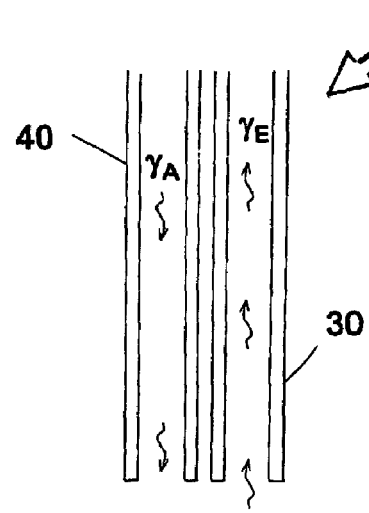
Figure 7:
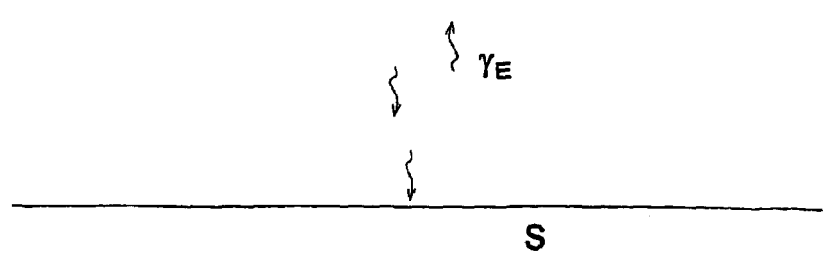
Figure 8:
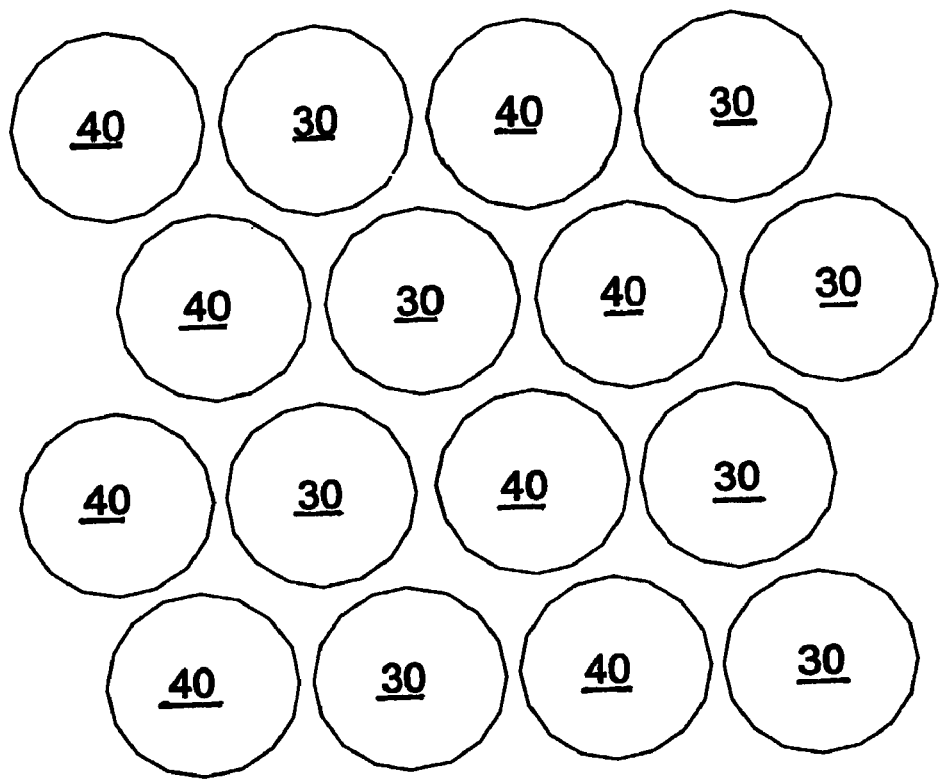
Figure 9:
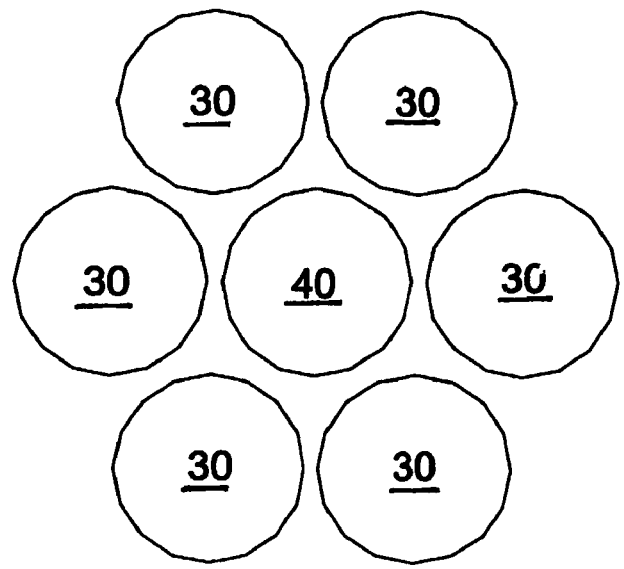
Figure 10:
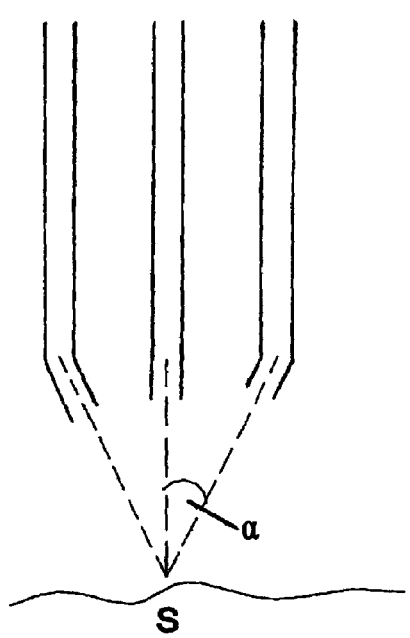
Figure 11:
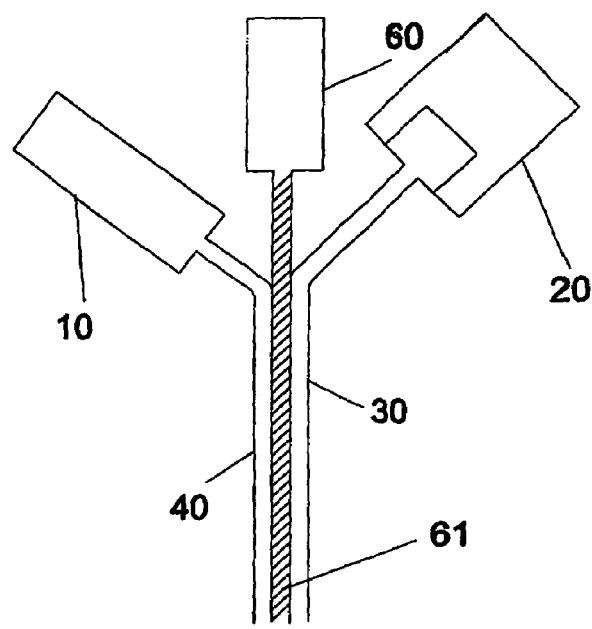
Figure 13:
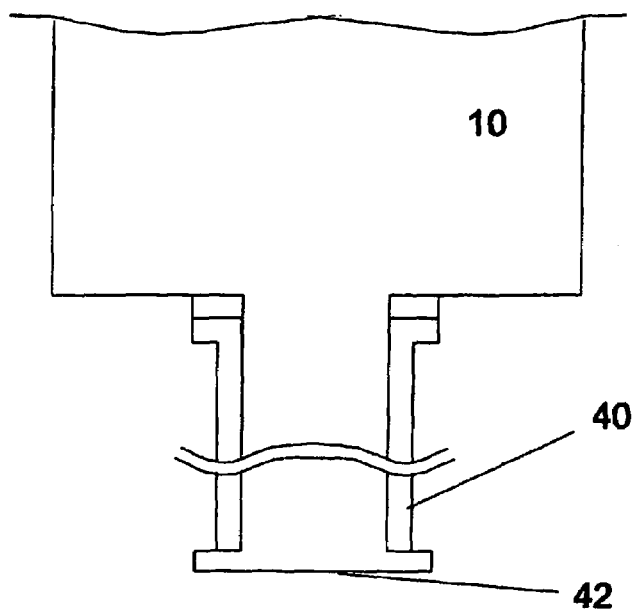
Figure 14A:
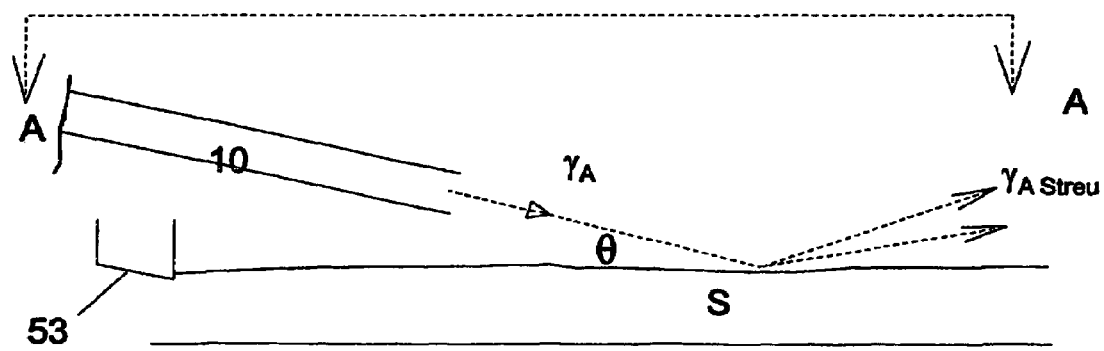
Figure 14B:
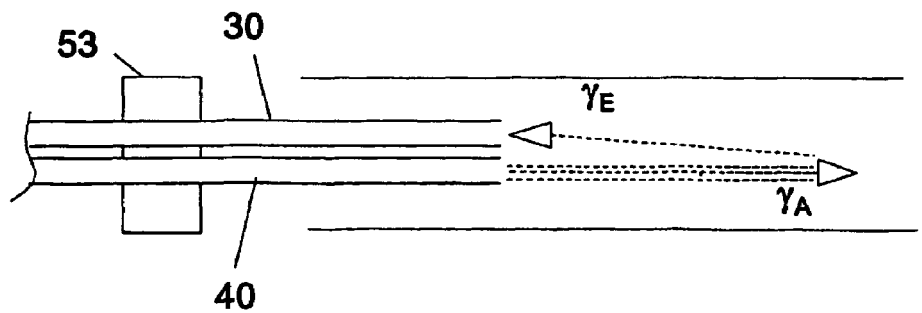
Figure 15:
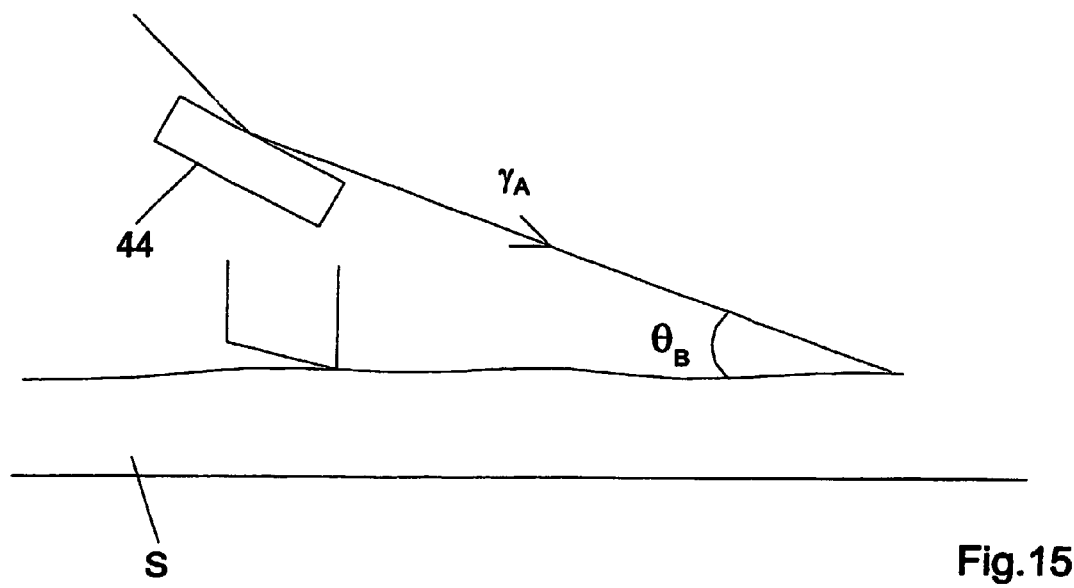
Figure 16:
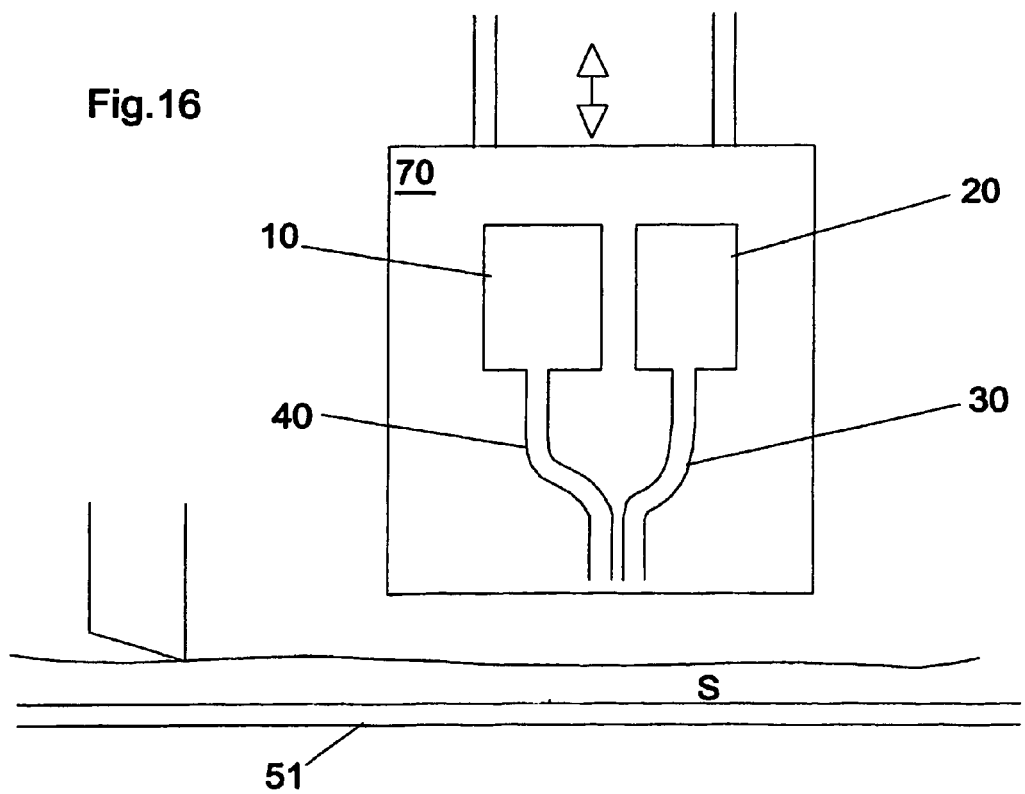

Further advantageous embodiments follow from the additional dependent claims and from the exemplary embodiments, described in further detail below, and by referring to the Figures with show in:

FIG. 1 A schematic representation of a first embodiment of the invention;

FIG. 2 An X-ray source with an X-ray focusing lens arranged in its beam path;

FIG. 3 A schematic representation of a second embodiment of the invention;

FIG. 4 An X-ray fluorescence detector with connected X-ray conductor in a schematic representation;

FIG. 5 An alternative embodiment to the one shown in FIG. 4;

FIG. 6 A schematic representation of an X-ray fluorescence detector and an X-ray source with separately connected X-ray conductors, wherein these conductors are combined to form a bundle;

FIG. 7 A partial view of FIG. 6;

FIG. 8 A bundle of X-ray conductors in a schematic cross-sectional view;

FIG. 9 A different embodiment showing a cross section through a bundle of X-ray conductors;

FIG. 10 An alternative embodiment to the one shown in FIG. 7;

FIG. 11 An embodiment as shown in FIG. 6, furthermore provided with a waveguide that is connected to a laser distance meter;

FIG. 12 A schematic representation of a measuring device according to prior art;

FIG. 13 An X-ray source with an X-ray conductor and a wavelength filter;

FIG. 14a A device showing a flat angle of incidence for the radiation;

FIG. 14b A view from above of the device shown in FIG. 14a, along the sight line A-A;

FIG. 15 A device where the polarized X-rays are radiated onto the substance;

FIG. 16 A displaceable measuring arrangement.

DESCRIPTION OF THE PREFERRED EMBODIMENTS

FIG. 1 shows a schematic representation of a first embodiment of the invention. A flow of the substance S to be measured is conveyed on a conveyor belt 51 past a measuring station. A leveling edge 53 is arranged upstream of the measuring station to ensure the most level surface possible for the substance to be measured at the measuring station. For this example, the measuring station consists of an X-ray tube 10, an X-ray fluorescence detector 20 and a first X-ray conductor that is connected to the radiation inlet for the X-ray fluorescence detector and which takes the form of a first glass capillary 30. Radiation-conducting glass capillaries of this type are commercially available.

The exciting X-radiation ($Y_A$) from the X-ray tube 10 is radiated onto the substance surface and generates in this substance characteristic excitation states for elements therein. The recombination of the excited states occurs partially radiating, wherein for the applications of interest herein, the $K_\alpha$ transition is frequently observed and with heavy elements the $L_\alpha$ transition. The radiation emission ($Y_E$) is generally isotropic, thus causing the radiation intensity to decrease with $1/r^2$ without taking into account the absorption in air. To obtain the strongest possible signal, the frontal end 30a of the first glass capillaries is positioned as close as possible to the surface of the substance flow, which is possible without collision with the X-ray tube 10 or its beam path, since glass capillaries 30 of this type can have a relatively thin design. Within the first glass capillaries 30, the entering X-rays propagate via total reflection along the walls, so that only an absorption-caused intensity loss occurs. As a result, the X-ray fluorescence detector 20 can be arranged relatively far from the surface of the substance S to be measured. We will come back at a later time to the problem of minimizing the absorption within the glass capillaries.

FIG. 2 shows an improved embodiment as compared to the example shown in FIG. 1, wherein an X-ray split lens 12 is disposed between the X-ray tube 10 and the surface of the substance S to be measured, so as to create a parallel alignment of the incident X-rays. On the one hand, this has the advantage that the intensity can be increased in the region of interest on the substance while the X-ray tube output remains the same. On the other hand, it causes the intensity on the surface of the substance to remain the same, even if the substance has an uneven surface. As a result, the reproducibility of the measuring result is improved.

FIG. 3 shows a second exemplary embodiment of the invention with a substance flow, in particular hot slag, sliding down a slide 55. A certain amount of the slag is removed continuously via an opening in this slide 55 and the rotary table 56 and is supplied to the measuring station, wherein the substance on the rotary table is also leveled by means of a leveling edge. However, the respective leveling edge is not located in the drawing plane and is therefore not shown herein. Once it passes by the measuring station, the respective substance is again supplied to the main flow on the slide 55 with the aid of a stripper that is also not shown.

The rotary table for this exemplary embodiment is located within a shielding housing 58, which also has relatively high temperatures as a result of the high temperatures of the slag to be measured. For that reason, the X-ray tube 10 as well as the X-ray fluorescence detector 20 and all components of the evaluation electronics are arranged outside of the shielding housing 58. The X-ray conductors, in this case the first glass capillary 30 and the second glass capillary 40, are used for feeding in and feeding out the X-radiation. It must be emphasized that in place of a first glass capillary, a bundle of first glass capillaries can generally also be used. The same is true for the second glass capillaries.

A portion of the radiation generated by the X-ray tube 10 enters the second glass capillary 40 where it propagates essentially without losses. Some of the fluorescent radiation generated by the substance to be measured enters into the first glass capillary 30 and from there into the X-ray fluorescence detector 20 where it is measured. The X-ray fluorescence detectors, used herein, generally are provided with a semiconductor element, e.g. a Si-Pin semiconductor element 25 for this example. Semiconductor elements of this type generally can function only at relatively low temperatures and become dummy elements at extremely high heat. As previously mentioned, relatively high temperatures exist during the operation inside the shielded housing 58, thus heating up the shielding housing 58 that primarily consists of metal. A thermal shield 59 is therefore arranged between the shielding housing 58 and the X-ray fluorescence detector 20. This thermal shield 59 can function either by reflecting or absorbing the heat and can be composed, for example, of a heat-insulating material or can also be cooled actively, e.g. by means of a water cooling device. Owing to the fact that the glass capillaries used herein as X-ray conductors can also have a curved design without losing their capacity to conduct radiation, it is possible to remove the X-ray fluorescence detector 20 completely from the line of sight of the substance to be measured.

FIG. 4 shows a somewhat larger detail, albeit schematic, of an X-ray fluorescence detector design with connected first glass capillary. As previously mentioned, the measuring of X-ray fluorescent radiation with low energy, in particular less than 2 keV, is a problem because the absorption in air is extremely high. It is therefore suggested that first glass capillaries 30 be filled with a lightweight gas, particularly helium. For this, we suggest connecting the first glass capillary 30 via a connecting flange 29 to the housing 22 of the X-ray fluorescence detector 20, such that the first glass capillary 30 and the inside of the housing 22 form a joint, helium-gas filled space. In axial extension of the first glass capillary 30, a semiconductor element is disposed inside the housing 22, for example a Si-Pin semiconductor element 25, which is preferably cooled with a Peltier cooling element 26. A current and signal supply line 27 connects the semiconductor element to the triggering and evaluation electronics.

To prevent the helium filling from escaping, the first glass capillary 30 is provided with a thin window 30b at the front end 30a, for example in the form of a beryllium film. This window furthermore prevents dirt particles from entering, which could reduce or destroy he X-ray conductivity of the first glass capillaries 30. To keep the absorption low, the beryllium film used for the window must be relatively thin.

FIG. 5 shows an alternative embodiment to FIG. 4, wherein the insides of the glass capillary 30 and the housing 22 form a joint space for the gas. However, a window for closing off the first glass capillary 30 was omitted in this case and the complete arrangement is constantly flushed with helium. The housing 22 is connected to a helium source 28 for this. The advantage of this arrangement is that a relatively sensitive window can be omitted. The helium flowing through the arrangement also prevents dirt particles from entering the glass capillary.

As previously mentioned, the glass capillaries used here as X-ray conductors can be bent up to a certain degree without resulting in the loss of X-ray conductivity. The glass capillaries used can therefore be combined into bundles, as shown in FIG. 6. The X-ray tube 10 and the X-ray fluorescence detector 20 can be spatially separated, but the end sections of the two glass capillaries 30 and 40 can be positioned close to each other and can extend parallel; see also FIG. 7. A precisely defined geometry can thus be created and, in particular, the measuring operation becomes relatively insensitive to the change in height of the substance flow, generally unavoidable with large-grain substances, owing to the fact that the feed-in direction as well as the emission direction for the X-rays is nearly perpendicular.

In principle, it is possible to bundle an optional number of glass capillaries and not just two glass capillaries. FIG. 8 shows a cross section through a bundle of this type where the glass capillaries are arranged in a matrix. First glass capillaries 30, which conduct the emitted fluorescence radiation toward the X-ray fluorescence detector 20, alternate with second glass capillaries 40, which conduct the X-ray radiation from the X-ray tube 10 to the substance to be measured, thus making it possible to achieve a relatively large yield of the emitted radiation.

FIG. 9 shows an exemplary embodiment for which a second glass capillary 40 is surrounded by several first glass capillaries 30. This arrangement also functions to capture as many emitted gamma quanta as possible and feed those to the X-ray fluorescence detector.

As alternative to the embodiment shown in FIG. 9, FIG. 10 shows that it is possible to slightly angle the first glass capillaries 30, relative to the second glass capillaries 40, so that the axes of all glass capillaries intersect at one point, namely the surface of the substance to be measured. Thus, if the surface position of the substance to be measured can be defined precisely, a further increase in the radiation yield can be achieved.

To evaluate the measuring results, it is important to know the precise location of the substance surface. The integration of a laser distance meter 60 into the existing measuring device is therefore also suggested, wherein the feed-in and feed-out of the laser radiation preferably occurs via a waveguide 61 that forms a bundle with the existing glass capillaries. As a result, the relative position of all components to each other is completely defined and no local offset or time offset occurs in the distance measurement relative to the X-ray fluorescence measuring; see FIG. 11.

Conveyor belts and rotary tables are used as transporting devices for the exemplary embodiments shown herein. However, it is clear that other types of conveying devices can also be used, for example tubes or grooves for the measuring of liquid substances.

Furthermore shown are options for reducing the background of the measured signal, which can be of particular importance when detecting lightweight elements since the intensity of the $K_\alpha$ radiation measured herein is often relatively low and can be covered almost completely by the background.

FIG. 13 shows a first option for reducing the background. A wavelength filter 42 is arranged in the beam path for the exciting X-rays. This wavelength filter 42 is selected so as to essentially permit only the passage of X-rays with an energy higher or equal to the lowest, desired excitation energy. For the exemplary embodiment shown herein, the wavelength filter 42 simultaneously functions to close off the second glass capillaries 40, for which the opposite ends are connected to the X-ray tube 10. Alternatively, one or several monochromatic illuminators can also be used in place of a waveguide.

FIGS. 14a and 14b show an alternative or additional option for reducing the measuring background, wherein the exciting X-rays are radiated with a flat angle θ onto the substance and the first glass capillary 30, which captures a portion of the fluorescent radiation, is essentially positioned at the same angle θ to the sample surface and extends parallel to the beam axis for the exciting X-rays, in this case parallel to the second glass capillary 40. As a result of this parallel guidance, this arrangement is also relatively insensitive to fluctuations in height of the substance surface.

Non-absorbed X-rays are scattered primarily in forward direction, so that only a small portion of these can enter the first glass capillary 30. Since the fluorescence is primarily isotropic, no reduction in the strength of the measured signal occurs, but a considerable reduction in the background.

The above-described effect can be further improved by polarizing the exciting X-rays by means of a polarizer 44 before they arrive at the substance surface and by radiating them at the Brewster angle $\theta_B$ onto the substance to be analyzed. As a result, the share of scattered X-rays can again be reduced considerably; see FIG. 15.

FIG. 16 shows that it is possible to have a very flexible design of the device according to the invention while retaining a high precision. For this, the X-ray tube 10, the X-ray fluorescence detector 20 and the respective X-ray conductors, a first glass capillary 30 and a second glass capillary 40 in this case, are arranged on an at least one-dimensionally displaceable carriage 70, so that the ideal position relative to the substance surface can be adjusted as needed without requiring an involved adjustment of the X-ray conductors relative to each other. The ability to pivot in a vertical plane can also be provided in addition to or alternative to a vertical mobility.

The invention claimed is:

1. A device for realizing an online element analysis for a substance to be measured that is conveyed past or flows past a measuring station, said device comprising:
    a conveying device for the substance to be measured; and
    the measuring station, further comprising an X-ray source and an X-ray fluorescence detector having a radiation inlet,
    wherein a first X-ray conductor extends from the radiation inlet of the X-ray fluorescence detector in a direction of the conveying device,
    wherein a second X-ray conductor extends from the X-ray source in the direction of the conveying device,
    wherein at least one of the first and the second X-ray conductor comprises at least one hollow tube,
    wherein the at least one hollow tube comprises a plurality of hollow tubes and at least one of the plurality of hollow tubes is connected to a helium source and is flushed with helium,
    wherein axes of the X-ray conductors are parallel to each other at ends of said X-ray conductors facing the conveying device.

2. A device for realizing an online element analysis for a substance to be measured that is conveyed past or flows past a measuring station, said device comprising:
    a conveying device for the substance to be measured; and
    the measuring station, further comprising an X-ray source and an X-ray fluorescence detector having a radiation inlet,
    wherein a first X-ray conductor extends from the radiation inlet of the X-ray fluorescence detector in a direction of the conveying device,
    further comprising a distance sensor for measuring a height of a sample surface,
    wherein the distance sensor is a laser distance sensor,
    wherein a waveguide is connected to the laser distance sensor to permit remote distance measurement,
    wherein the waveguide forms a bundle together with the first X-ray conductor.

3. The device according to claim 1 wherein a second X-ray conductor extends from the X-ray source in the direction of the conveying device.

4. The device according to claim 3 wherein at least one of the first and the second X-ray conductor comprises one or more hollow tubes.

5. The device according to claim 4, wherein at least one hollow tube is at least partly made of glass.

6. The device according to claim 5, wherein at least one hollow tube is a glass capillary.

7. The device according to claim 4, wherein at least one of the hollow tubes is provided with a window at an end thereof facing the conveying device.

8. The device according to claim 4, wherein at least one of the hollow tubes is filled with hydrogen or helium.

9. The device according to claim 8, wherein several first and several second X-ray conductors exist and are combined so as to create a matrix-type structure.

10. The device according to claim 8, wherein at least one second X-ray conductor and plural first X-ray conductors are provided, said plural first X-ray conductors arranged around the at least one second X-ray conductor, at least at an end of said at least one second X-ray conductor facing the conveying device.

11. The device according to claim 8, wherein axes of the second X-ray conductor and the first X-ray conductor jointly enclose an acute angle in the direction of the conveying device.

12. The device according to claim 4, wherein at least one of the hollow tubes is connected to a helium source and is flushed with helium.

13. The device according to claim 3, wherein the first and the second X-ray conductors are combined in such a way that a bundle of at least two X-ray conductors is formed at ends of the X-ray conductors facing the conveying device.

14. A device for realizing an online element analysis for a substance to be measured that is conveyed past or flows past a measuring station, said device comprising:
- a conveying device for the substance to be measured; and
- the measuring station, further comprising an X-ray source and an X-ray fluorescence detector having a radiation inlet,
- wherein a first X-ray conductor extends from the radiation inlet of the X-ray fluorescence detector in a direction of the conveying device,
- wherein a second X-ray conductor extends from the X-ray source in the direction of the conveying device,
- wherein at least one of the first and the second X-ray conductor comprises at least one hollow tube,
- wherein axes of the X-ray conductors are parallel to each other at ends of said X-ray conductors facing the conveying device.

15. The device according to claim 14, wherein at least one thermal shield is disposed between the X-ray fluorescence detector and the conveying device.

16. The device according to claim 14, further comprising a distance sensor for measuring a height of a sample surface.

17. The device according to claim 16, wherein the distance sensor is a laser distance sensor.

18. The device according to claim 17, wherein a waveguide is connected to the laser distance sensor to permit remote distance measurement.

19. The device according to claim 14, wherein an X-ray split lens for parallel alignment of X-rays is disposed in a beam path from the X-ray source.

20. The device according to claim 14, Wherein a filter or a monochromatic element is arranged in a beam path from the X-ray source.

21. The device according to claim claim 20, wherein the filter functions as a window.

22. The device according to claim 14, wherein the first X-ray conductor and exciting radiation from the X-ray source are at a substantially equal angle relative to a sample surface.

23. The device according to claim 22, wherein the substantially equal angle is a flat angle.

24. The device according to claim 23, wherein the flat angle corresponds to a Brewster angle for radiation polarized by a polarizer.

25. The device according to claim 14, wherein a polarizer is arranged in a beam path from the X-ray source.

26. The device according to claim 14, wherein the measuring station is arranged on a traversing and/or pivoting carriage.

* * * * *